United States Patent
Lichy et al.

(10) Patent No.: US 10,699,392 B2
(45) Date of Patent: Jun. 30, 2020

(54) CONTRAST-ENHANCED REPRODUCTION OF SPECTRAL CT IMAGE DATA

(71) Applicant: Siemens Healthcare GmbH, Erlangen (DE)

(72) Inventors: Matthias Lichy, Nuremberg (DE); Sebastian Schmidt, Weisendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 50 days.

(21) Appl. No.: 15/924,470

(22) Filed: Mar. 19, 2018

(65) Prior Publication Data
US 2018/0276802 A1 Sep. 27, 2018

(30) Foreign Application Priority Data

Mar. 21, 2017 (EP) ..................................... 17162007

(51) Int. Cl.
| | |
|---|---|
| *G06T 5/00* | (2006.01) |
| *A61B 6/00* | (2006.01) |
| *A61B 6/03* | (2006.01) |
| *G06T 7/00* | (2017.01) |
| *G06T 5/50* | (2006.01) |

(52) U.S. Cl.
CPC ............. *G06T 5/009* (2013.01); *A61B 6/032* (2013.01); *A61B 6/5217* (2013.01); *G06T 5/007* (2013.01); *G06T 5/50* (2013.01); *G06T 7/0012* (2013.01); *G06T 2207/10081* (2013.01); *G06T 2207/20081* (2013.01); *G06T 2207/20208* (2013.01); *G06T 2207/30096* (2013.01)

(58) Field of Classification Search
CPC ........... G06T 5/009; G06T 5/007; G06T 5/50; G06T 7/0012; A61B 6/5217; A61B 6/032
See application file for complete search history.

(56) References Cited

U.S. PATENT DOCUMENTS

| | | |
|---|---|---|
| 2005/0163283 A1 | 7/2005 | Bruder |
| 2006/0109949 A1 | 5/2006 | Tkaczyk |
| 2009/0052612 A1* | 2/2009 | Wu ......................... A61B 6/032 378/5 |

(Continued)

OTHER PUBLICATIONS

Qingsong Yang et al "Material decomposition with dual energy CT", IEEE 2015. (Year: 2015).*

(Continued)

*Primary Examiner* — Leon Flores
(74) *Attorney, Agent, or Firm* — Harness, Dickey & Pierce, P.L.C.

(57) ABSTRACT

A method is for setting a contrast of a multi-energy CT image representation. In an embodiment of the method, a plurality of multispectral image datasets of an examination region of a patient are received. Furthermore, an automated identification of a structure to be examined is achieved based upon the multispectral image datasets and an automated combining of the differently weighted multispectral image datasets is accomplished such that the contrast between the structure to be examined and its environment is improved compared to a uniform weighting. Further, a multi-energy CT imaging method is described. An image setting device is also described. In addition, a computed tomography system is described.

20 Claims, 2 Drawing Sheets

(56) References Cited

U.S. PATENT DOCUMENTS

2013/0101082 A1* 4/2013 Jordan .................. A61B 6/4035
378/19
2017/0011185 A1* 1/2017 Schweizer ............ G06F 19/321

OTHER PUBLICATIONS http://web.archive.org/web/20160509103806/http://www.olympus.de/medical/de/medical_systems/applications/gastroenterology_1/narrow_band_imaging_nbi_in_gastroenterology/narrow_band_imaging_nbi_2.jsp; 2016.

Glocker B. et al: "Random Forests for Localization of Spinal Anatomy"; In: "Medical Image Recognition, Segmentation and Parsing", Elsevier, XP055391982, .ISBN: 978-0-12-802581-9; pp. 93-110, DOI: 10.1016/B978-0-12-802581-9.00005-6,; 2015.

Schmidt Taly: "Optimal image-based weighting for energy-resolved CT", Medical Physics, AIP, Melville, NY, US, Bd. 36, Nr. 7, pp. 3018-3027, XP012130093, ISSN: 0094-2405, DOI: 10.1118/1.3148535; 2009.

Mertens T et al: "Exposure Fusion", Computer Graphics and Applications, 2007. PG '07. 15th Pacific Conference On, IEEE, Piscataway, NJ, USA, pp. 382-390, XP031338475; ISBN: 978-0-7695-3009.3; 2007.

Cramer Todd W et al: "A primer on the use of dual-energy CT in the evaluation of commonly encountered neoplasms", Abdominal Radiology, Springer US, New York, Bd. 41, Nr. 8, pp. 1618-1631, XP036021565, ISSN: 2366-004X, DOI: 10.1007/S00261-016-0707-X; 2016.

Rajbhandary Paurakh L et al: "Conventional CT images from spectral measurements", Progress in Biomedical Optics and Imaging, SPIE—International Society for Optical Engineering, Bellingham, WA, US, Bd. 9783, Seiten 97831Q-97831Q, XP060066098, ISSN: 1605-7422,. DOI: 10.1117/12.2216988; ISBN: 978-1-5106-0027-0; 2016.

Lifeng Yu et al: "Dual-Energy CT-Based Monochromatic Imaging", American Journal of Roentgenology, Bd. 199, Nr. 5 supplement, pp. S9-SI5, XP055392243, US ISSN: 0361-803X, DOI: 10.2214/AJR.12.9121; 2012.

Extended European Search Report dated Aug. 2, 2017.

* cited by examiner

CONTRAST-ENHANCED REPRODUCTION OF SPECTRAL CT IMAGE DATA

PRIORITY STATEMENT

The present application hereby claims priority under 35 U.S.C. § 119 to European patent application number EP 17162007.3 filed Mar. 21, 2017, the entire contents of which are hereby incorporated herein by reference.

FIELD

At least one embodiment of the invention generally relates to a method for setting a contrast of a multi-energy CT image representation. At least one embodiment of the invention also generally relates to a multi-energy CT imaging method. At least one embodiment of the invention further generally relates to a setting device. In addition, at least one embodiment of the invention generally relates to a computed tomography system.

BACKGROUND

State-of-the-art imaging techniques are often enlisted as an aid in order to generate two- or three-dimensional image data, which can be used for visualizing an imaged examination object, as well as for other applications besides.

The imaging techniques are often based on the detection of x-ray radiation, during which process primary data known as projection measurement data is generated. Projection measurement data can be acquired with the aid of a computed tomography system (CT system), for example. In CT systems, a combination of x-ray source and oppositely disposed x-ray detector arranged on a gantry typically rotates around a measurement chamber in which the examination object (referred to hereinbelow without loss of generality as the patient) is situated. In this arrangement, the center of rotation (also called the "isocenter") coincides with an axis called the system axis z. In the course of one or more revolutions, the patient is irradiated with x-ray radiation from the x-ray source, projection measurement data or x-ray projection data being captured with the aid of the oppositely disposed x-ray detector.

The generated projection measurement data is dependent in particular on the design of the x-ray detector. Typically, x-ray detectors comprise a plurality of detection units, which in most cases are arranged in the form of a regular pixel array. Each of the detection units generates a detection signal for x-ray radiation that is incident on the respective detection unit, the detection signal being analyzed in respect of intensity and spectral distribution of the x-ray radiation at specific time instants in order to draw inferences about the examination object and to generate projection measurement data.

The measured intensities correspond to quantities called attenuation values, which are expressed in what are termed Hounsfield units (abbreviated to HU). Numeric equivalents of the attenuation values lie between −1000 and several thousand in the positive range. Grayscale values are assigned to the HU values in CT imaging. Since human beings are unable to differentiate such a large number of grayscales, the technique known as "windowing" was introduced in which a selectable part of the HU scale is linearly mapped to grayscales from white to black. The user can freely set specific windowing parameters, the center and width of the window being specified in HUs. All HU values within the window are then mapped to the available grayscale levels, of which the human eye is able to distinguish around 60 values. The HU values chosen for center and width are in this case tailored to the respective examination region and examination purpose. For example, the choice of the HU values is dependent on the organs that are to be examined and on the clinically relevant density values associated therewith. There are considerable differences between these values clinically set as "windows", according to the field of application.

A novel form of CT imaging is the technique known as spectral CT imaging. With this, x-ray beams are detected resolved according to x-ray energy. Since photons of different energy are absorbed differently by different materials, different materials can be detected separately via such an imaging method. An example of this is the visualization of the distribution of contrast agent taken up in vessels. False color renditions, as they are called, are generated for such a visualization.

Given four or more resolved photon energies, image representations are produced in which quite different images are generated, depending on the weighting of the energy bands. Compared to windowing, instead of a linear one-dimensional problem in the conversion of grayscale values, a multidimensional problem exists in the weighting of the individual energy bands. It is therefore very difficult or indeed well-nigh impossible for a user to set a contrast that is ideal for his or her purposes.

In photographic imaging, there are contrast selection methods in which certain parts of the color spectrum are absorbed with the aid of a color filter in order to highlight contrasts in other parts of the spectrum. In black-and-white photography, for example, a yellow filter is used for rendering clouds such that the sky appears darker and the white clouds stand out more distinctly. Even in the case of the three-color system of human vision, however, such a choice of contrast works only in a small number of applications.

In endoscopy, imaging is achieved with the aid of a technique known as "narrow band imaging". Such a technique is described in https://www.olympus.de/medical/de/medical systems/applications/gastroenterology_1/narrow_band_imaging_nbi_in_gastroenterology/narrow_band_imaging_nbi_2.jsp. This entails filtering out certain energy bands so that the remaining energy components yield a maximum contrast for certain structures, for example blood vessels as opposed to mucous membrane. Such an approach works well in gastroenterology because the same contrasts are required in all situations.

However, a "unity filter" of the type is not suitable for radiology, with its much greater variability of structures to be visualized, for example lesions.

SUMMARY

At least one embodiment of the invention discloses a method and an arrangement for setting a suitable contrast for the representation of weighted images on the basis of multi-energy CT imaging.

At least one embodiment is directed to a method for setting a contrast of a multi-energy CT image representation, a multi-energy CT imaging method, an image setting device, and/or a computed tomography system.

In at least one embodiment of the inventive method for setting a contrast of a multi-energy CT image representation, a plurality of multispectral image datasets of an examination region of a patient are received. The multispectral image datasets may for example have been acquired currently within the scope of an imaging method and reconstructed by a reconstruction unit and subsequently directly processed further with the aid of at least one embodiment of the inventive method.

At least one embodiment of the inventive image setting device has an input interface for receiving a plurality of multispectral image datasets of an examination region. The inventive image setting device additionally comprises an identification unit enabling the automated identification of a structure to be examined on the basis of the multispectral image datasets. Also part of at least one embodiment of the inventive image setting device is a combination unit for the automated combining of the differently weighted multispectral image datasets in such a way that the contrast between the structure to be examined and its environment is improved compared to a uniform weighting.

At least one embodiment of the inventive computed tomography system comprises a scan unit for acquiring projection measurement data of an examination region of a patient. Part of at least one embodiment of the inventive x-ray imaging device is a control device for controlling the scan unit and for generating image data on the basis of the acquired projection measurement data. At least one embodiment of the inventive x-ray imaging device also comprises an inventive image setting device.

A largely software-based implementation of at least one embodiment has the advantage that computed tomography systems already in use previously in the prior art can also be easily upgraded by way of a software update in order to operate in the manner according to at least one embodiment of the invention. In that respect, the object is also achieved by way of a corresponding computer program product having a computer program which can be loaded directly into a memory device of a computed tomography system, and having program sections for the purpose of performing all steps of at least one embodiment of the inventive method when the computer program is executed in the computed tomography system.

As well as the computer program, such a computer program product may, where appropriate, comprise additional constituent parts such as e.g. documentation and/or additional components, including hardware components, such as e.g. hardware keys (dongles, etc.) to allow use of the software.

A computer-readable medium, for example a memory stick, a hard disk or some other transportable or permanently installed data carrier, on which the program sections of the computer program that can be read in and executed by a computer unit are stored, may be used for transporting the computer program product to a memory device of such a computed tomography system and/or for storing the same on the computed tomography system. For this purpose, the computer unit may have e.g. one or more cooperating microprocessors or the like.

The claims and the following description in each case contain particularly advantageous embodiments and developments of the invention. In particular, the claims of one claims category can at the same time also be developed analogously to the dependent claims of a different claims category or the associated parts of the description. Furthermore, the various features of different example embodiments and claims may also be combined within the scope of the invention to create new example embodiments.

BRIEF DESCRIPTION OF THE DRAWINGS

The invention is explained once again in more detail below with the aid of example embodiments and with reference to the attached figures, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment of the inventive method for setting a contrast of a multi-energy CT image representation, a plurality of multispectral image datasets of an examination region of a patient are received. The multispectral image datasets may for example have been acquired currently within the scope of an imaging method and reconstructed by a reconstruction unit and subsequently directly processed further with the aid of at least one embodiment of the inventive method.

Alternatively, the multispectral image datasets may also originate from a database or a data memory in which they have been buffered for a relatively long period of time. A structure that is to be examined is then identified in an automated manner on the basis of the multispectral image datasets. By an identification is to be understood that a position of a structure has been determined and the structure is assigned to a predetermined classification. As a structure is to be understood a subregion differing from its environment in an examination region of a patient. Finally, the multispectral image datasets, having been assigned different weightings, are automatically combined in such a way that the contrast between the structure to be examined and its environment is improved compared to a uniform weighting.

Advantageously, the ability to recognize the structure to be examined is improved, while the automated procedure speeds up and simplifies the preprocessing and editing process. With a plurality of spectral image datasets, an optimal weighting of the individual image datasets becomes very labor-intensive and time-consuming to achieve manually and practically impossible to realize due to the multiplicity of variation possibilities even for a spectral resolution of a minimum of four photon energies. Advantageously, the inventive setting method also allows a fast setting of contrasts of multi-energy CT image representations having a multiplicity of different x-ray energy spectra. Since the execution of the inventive method is automated, the method can also be applied when no specially qualified personnel are available for evaluating the image.

In at least one embodiment of the inventive multi-energy CT imaging method, a plurality of multispectral projection measurement datasets of an examination region are acquired. This is followed by the reconstruction of a plurality of multispectral image datasets on the basis of the multispectral projection measurement datasets. In addition, an image representation that is improved in terms of contrast is generated on the basis of the reconstructed multispectral image datasets using an inventive method for setting a contrast of a multi-energy CT image representation.

At least one embodiment of the inventive image setting device has an input interface for receiving a plurality of multispectral image datasets of an examination region. The inventive image setting device additionally comprises an identification unit enabling the automated identification of a structure to be examined on the basis of the multispectral image datasets. Also part of at least one embodiment of the inventive image setting device is a combination unit for the automated combining of the differently weighted multispectral image datasets in such a way that the contrast between the structure to be examined and its environment is improved compared to a uniform weighting.

At least one embodiment of the inventive computed tomography system comprises a scan unit for acquiring projection measurement data of an examination region of a patient. Part of at least one embodiment of the inventive x-ray imaging device is a control device for controlling the scan unit and for generating image data on the basis of the acquired projection measurement data. At least one embodiment of the inventive x-ray imaging device also comprises an inventive image setting device.

Most of the main components of at least one embodiment of the inventive image setting device can be embodied in the form of software components. This relates in particular to the identification unit and the combination unit. In principle, however, some of these components may also be realized in the form of software-assisted hardware, for example FPGAs or the like, in particular when there is a requirement for particularly fast calculations. Similarly, the required interfaces may be embodied as software interfaces, for example when it is simply a matter of importing data from other software components. They may, however, also be embodied as hardware-based interfaces which are controlled by suitable software.

A largely software-based implementation has the advantage that computed tomography systems already in use previously in the prior art can also be easily upgraded by way of a software update in order to operate in the manner according to at least one embodiment of the invention. In that respect, the object is also achieved by way of a corresponding computer program product having a computer program which can be loaded directly into a memory device of a computed tomography system, and having program sections for the purpose of performing all steps of at least one embodiment of the inventive method when the computer program is executed in the computed tomography system.

As well as the computer program, such a computer program product may, where appropriate, comprise additional constituent parts such as e.g. documentation and/or additional components, including hardware components, such as e.g. hardware keys (dongles, etc.) to allow use of the software.

A computer-readable medium, for example a memory stick, a hard disk or some other transportable or permanently installed data carrier, on which the program sections of the computer program that can be read in and executed by a computer unit are stored, may be used for transporting the computer program product to a memory device of such a computed tomography system and/or for storing the same on the computed tomography system. For this purpose, the computer unit may have e.g. one or more cooperating microprocessors or the like.

The claims and the following description in each case contain particularly advantageous embodiments and developments of the invention. In particular, the claims of one claims category can at the same time also be developed analogously to the dependent claims of a different claims category or the associated parts of the description. Furthermore, the various features of different example embodiments and claims may also be combined within the scope of the invention to create new example embodiments.

In an embodiment of the inventive method for setting a contrast of a multi-energy CT image representation, the structure to be examined comprises a lesion.

If the contrast of a lesion is improved compared to the environment, the lesion can be more easily classified and as a result it is easier to reach a prognosis with regard to its severity.

Alternatively, the structure may also comprise an anatomical structure, such as an organ, a vessel structure or a bone structure, for example.

In an embodiment of the inventive method for setting a contrast of a multi-energy CT image representation, the structure to be examined is identified with the aid of a method based on machine learning. Such a machine learning-based method can be trained for example with the aid of a relatively large number of annotated image datasets in order to enable automatic detection of a predetermined structure, for example a lesion, in the image. Such a training phase permits an automated identification method to specify the features relevant to an identification in a flexible manner as a function of the database used for the training.

Such a method is therefore particularly widely applicable, since it does not rely on rigid rules or models that have been specified in advance.

In an embodiment, the inventive method for setting a contrast of a multi-energy CT image representation, the structure to be examined is preferably identified with the aid of a method based on computer-assisted detection. Methods of this kind help in the process of searching image data obtained from computed tomography for typical patterns.

In a particularly advantageous embodiment of the inventive method for setting a contrast of a multi-energy CT image representation, the different weighting of the combination of multispectral image datasets is determined on the basis of a learning system which is trained with the aid of corrections by the user. The learning process applied in this case is also referred to as "deep learning" or "machine learning". Advantageously, the contrast setting in advance via a training process can be customized to suit a user's individual requirements and preferences.

Within the scope of an embodiment of the inventive method for setting a contrast of a multi-energy CT image representation, the different weighting of the combination of multispectral image datasets is determined using a rule-based approach. What is to be understood as rule-based weighting is a method that is at least partially based on a pre-specified model. Advantageously, such a system can be deployed quickly, since it is based on fixed rules and does not have to be trained first.

In a further embodiment of the inventive method for setting a contrast of a multi-energy CT image representation, the differently weighted combining of the multispectral image datasets includes a weighted addition of the multispectral image datasets. For example, a lesion may have been stained with iodine via an injection prior to the imaging. In such a case, the contrast of the lesion can be enhanced if portions of the spectral data lying as close as possible to the K-absorption edge of iodine, i.e. at an energy of approx. 33 keV, are weighted more heavily for the addition than other spectral components.

In a special embodiment of the inventive method for setting a contrast of a multi-energy CT image representation, the differently weighted combining of the multispectral image datasets includes a weighted subtraction of the multispectral image datasets. A subtraction can be useful for example for removing or at least reducing background structures from an image. If, for example, it were desired to visualize only the iodine distribution in an iodine-contrasted image representation, background areas can be eliminated by subtraction of different spectral components.

In an embodiment of the inventive method for setting a contrast of a multi-energy CT image representation, the weighted combining of the multispectral image datasets comprises a nonlinear transformation. An example of this is when the only data of an image dataset to be used is that which is associated with voxels whose signal intensity exceeds a defined threshold value. Another example is present when all voxels whose signal intensity exceeds a defined threshold value in a first image dataset obtain their contrast only from a second image dataset, and all voxels whose intensity lies below the threshold receive their contrast from a third image dataset.

In an embodiment of the inventive method for setting a contrast of a multi-energy CT image representation, the differently weighted multispectral image datasets are combined in such a way that the contrast between the structure to be examined and its environment is optimized. In this variant, the best possible contrast result is advantageously achieved through combination of the multispectral image datasets. For this purpose, an automated optimization method can for example be applied which determines an image representation having an optimal contrast, for example a maximally achievable contrast between the structure to be examined and its environment, with the aid of mathematical algorithms.

In an embodiment of the inventive method for setting a contrast of a multi-energy CT image representation, the multispectral image datasets are additionally combined with calculated image data. An example of calculated image data is a so-called iodine map, in which the content of iodine-containing contrast agent per voxel is determined and represented in false colors. Another example is an FFR calculation (FFR=fractional flow reserve), in which the flow resistance of blood vessels is calculated via a flow simulation and is likewise represented in a false color rendition. In this way, additional information can advantageously be displayed in a single image representation, thus facilitating an assessment for reaching a diagnosis.

Figure 1:
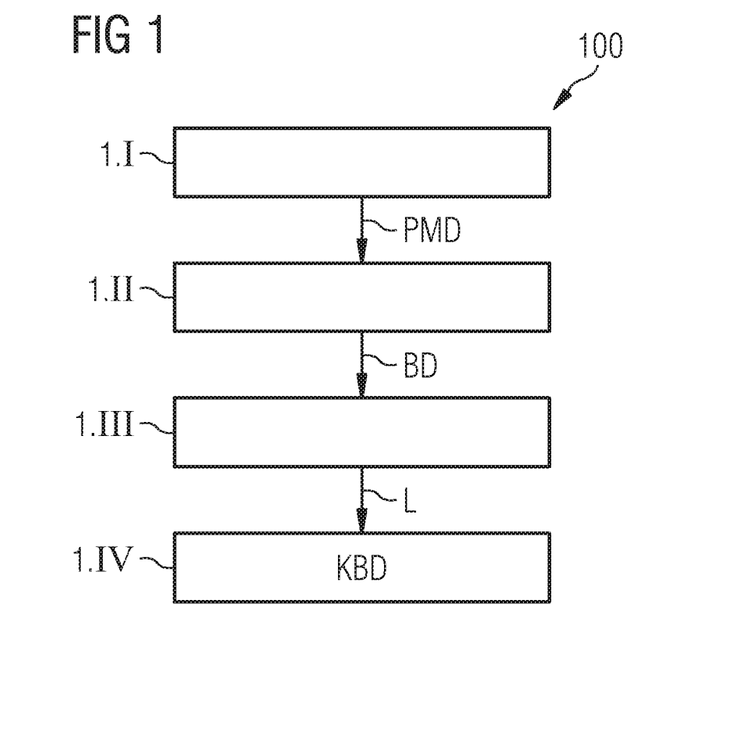
FIG. 1 shows a flowchart which illustrates a method for setting a contrast of a multi-energy CT image representation according to an example embodiment of the invention.

FIG. 1 shows a flowchart 100 illustrating a method for setting a contrast of a multi-energy CT image representation according to an example embodiment of the invention. Firstly, at step 1.I, a plurality of multispectral projection measurement datasets PMD of an examination region of a patient are acquired. Next, at step 1.II, a plurality of multispectral image datasets BD are reconstructed on the basis of the multispectral projection measurement datasets PMD. At step 1.III, a lesion L to be examined is identified in an automated manner on the basis of the multispectral image datasets BD. The identification can be achieved for example with the aid of an identification step which has been trained with the aid of a machine learning process to detect a pathology, in this case a lesion L, by automated means. At step 1.IV, the multispectral image datasets are then weighted in such a way that the contrast between the lesion L and its environment is increased compared to a uniform weighting. Such a lesion L may contain iodine as contrast agent, for example. In such a case, the contrast is enhanced if spectral components lying as close as possible to the K-absorption edge of iodine are weighted more heavily. This weighting can be rule-based, but may also be accomplished via a learning system which is continuously trained with the aid of user feedbacks. At step 1.IV, a combined image dataset KBD is therefore generated which exhibits an optimized contrast between the lesion L and its environment.

Figure 2:
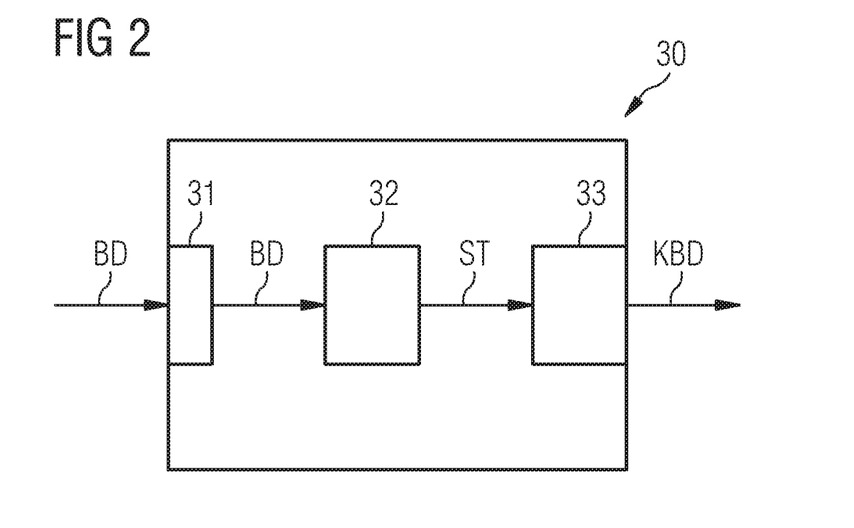
FIG. 2 shows a schematic representation of an image setting device according to an example embodiment of the invention.

FIG. 2 shows a schematic representation of an image setting device 30 according to an example embodiment of the invention. The image setting device 30 comprises an input interface 31 for receiving a plurality of multispectral image datasets BD of an examination region. From the input interface 31, the image data BD is transferred to an identification unit 32, which is configured to identify a structure ST to be examined, for example a lesion L, on the basis of the multispectral image datasets BD. After the identified structure ST has been marked, the image data BD is forwarded to a combination unit 33. The combination unit 33 is configured to perform a weighted combination of the multispectral image datasets BD in such a way that the contrast between the structure ST to be examined and its environment is improved compared to a uniform weighting.

Figure 3:
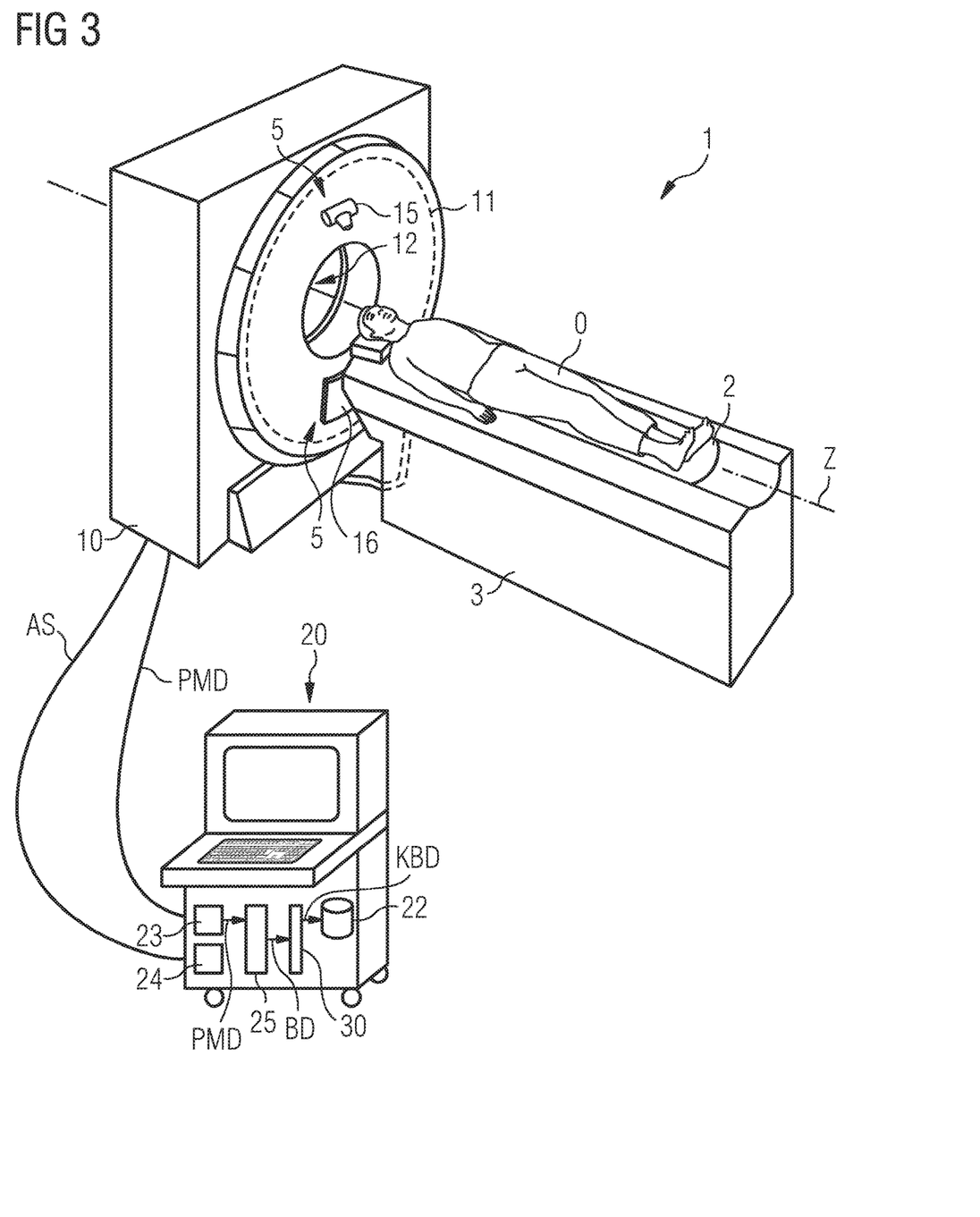
FIG. 3 shows a schematic representation of a computed tomography system according to an example embodiment of the invention.

FIG. 3 shows a computed tomography system 1 which comprises an image setting device 30 shown in detail in FIG. 2. The CT system 1 in this case consists substantially of a conventional scan unit 10 in which a projection data acquisition unit 5 mounted on a gantry 11 and comprising a quantum-counting detector 16 and an x-ray source 15 disposed opposite the quantum-counting detector 16 rotates around a measurement chamber 12. A quantum-counting detector has the ability to resolve captured x-ray beams in terms of the energy of the x-ray quanta. By way of such a quantum-counting detector, the absorption of different spectral components of the x-ray radiation can be measured simultaneously and resolved according to the x-ray energy.

Located in front of the scan unit 10 is a patient support device 3 or patient table 3, the upper part 2 of which can be maneuvered with a patient O positioned thereon toward the scan unit 10 in order to move the patient O through the measurement chamber 12 relative to the detector system 16. The scan unit 10 and the patient table 3 are controlled via a control device 20, from which there are transmitted, via a conventional control interface 24, acquisition control signals AS for the purpose of controlling the overall system in accordance with predefined measurement protocols in the traditional manner.

In the case of a spiral acquisition, a movement of the patient O along the z-direction, which corresponds to the system axis z lengthwise through the measurement chamber 12, and the simultaneous rotation of the X-ray source 15 result in a helical trajectory being produced for the X-ray source 15 relative to the patient O during the measurement. In parallel, the detector 16 constantly co-rotates as well opposite the X-ray source 15 in order to acquire projection measurement data PMD, which is then used to reconstruct volume and/or slice image data. Similarly, a sequential measurement method can also be performed in which a fixed position in the z-direction is approached and then the required projection measurement data PMD is acquired at the relevant z-position during one revolution, a partial revolution or several revolutions in order to reconstruct a slice image at the z-position or in order to reconstruct image data BD from the projection measurement data PMD of a plurality of z-positions.

At least one embodiment of the inventive method is basically also suitable for use on other CT systems, e.g. systems having a plurality of x-ray sources and/or detectors and/or having one detector forming a complete ring. The inventive method can, for example, also be applied to a system having a stationary patient table and a gantry moving in the z-direction (also known as a sliding gantry).

The projection measurement data PMD (also referred to in the following as raw data) acquired by the detector 16 is transferred to the control device 20 via a raw data interface 23. Following suitable preprocessing where appropriate (e.g. filtering and/or beam hardening correction), the raw data PMD is then processed further in an image reconstruction device 25, which in the present example embodiment is realized in the form of software on a processor in the control device 20. The image reconstruction device 25 reconstructs image data BD on the basis of the raw data PMD with the aid of a reconstruction method. A reconstruction method based on filtered back-projection may be used as the reconstruction method, for example.

The reconstructed image data BD is subsequently transferred to an image setting device 30, as is shown in detail in FIG. 2. On the basis of the reconstructed image data BD, the image setting device 30 generates combined image data KBD, which is weighted in the manner described in connection with FIGS. 1 and 2.

The combined image data KBD generated by the image setting device 30 is then stored in a memory 22 of the control device 20 and/or output in the usual way on the screen of the control device 20. The data can also be fed via an interface (not shown in FIG. 3) into a network connected to the computed tomography system 1, for example a radiological information system (RIS), and stored in a mass storage facility that is accessible there or output as images on printers or filming stations connected there. The data can thus be processed further in any desired manner and then stored or output.

Most or all of the components of the image setting device 30 may be realized in the form of software elements on a suitable processor. In particular, the interfaces between these components may also be embodied exclusively in software. All that is required is to provide means of access to suitable storage areas in which the data can be suitably buffered and retrieved and updated at any time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

In conclusion, it is pointed out once again that the methods and devices described in the foregoing are simply preferred example embodiments of the invention and that the invention may be varied by the person skilled in the art without leaving the scope of the invention as defined by the claims. It is also pointed out for the sake of completeness that the use of the indefinite articles "a" or "an" does not exclude the possibility that the features in question may also be present more than once. Similarly, the term "unit" does not rule out the possibility that the same consists of a plurality of components which, where necessary, may also be distributed in space.

What is claimed is:

1. A method for setting a contrast of a multi-energy CT image representation, the method comprising:
   receiving a plurality of multispectral image datasets of an examination region of a patient, the plurality of multispectral image datasets obtained by reconstruction based on multispectral projection measurement datasets;
   automatically identifying a structure to be examined based on the plurality of multispectral image datasets; and
   automatically combining differently weighted ones of the plurality of multispectral image datasets such that contrast between the structure to be examined and an environment of the structure to be examined is increased as compared to a uniform weighting.

2. The method of claim 1, wherein the structure to be examined includes a lesion.

3. The method of claim 2, wherein the structure to be examined is identified using a method based on machine learning.

4. The method of claim 2, wherein the structure to be examined is identified using a method based on computer-assisted detection.

5. The method of claim 2, wherein the plurality of multispectral image datasets are additionally combined with calculated image data.

6. The method of claim 1, wherein the structure to be examined is identified using a method based on machine learning.

7. The method of claim 1, wherein the structure to be examined is identified using a method based on computer-assisted detection.

8. The method of claim 1, wherein
   the automatically combining differently weighted ones of the plurality of multispectral image datasets is determined based on a learning system, and
   the learning system is trained by corrections by a user.

9. The method of claim 1, wherein the automatically combining differently weighted ones of the plurality of multispectral image datasets is determined using a rule-based approach.

10. The method of claim 1, wherein the automatically combining differently weighted ones of the plurality of multispectral image datasets includes a weighted addition of the plurality of multispectral image datasets.

11. The method of claim 1, wherein the automatically combining differently weighted ones of the plurality of multispectral image datasets includes a weighted subtraction of the plurality of multispectral image datasets.

12. The method of claim 1, wherein the automatically combining differently weighted ones of the plurality of multispectral image datasets includes a nonlinear transformation.

13. The method of claim 1, wherein the automatically combining differently weighted ones of the plurality of multispectral image datasets is accomplished such that the contrast between the structure to be examined and the environment of the structure to be examined is optimized.

14. The method of claim 1, wherein the plurality of multispectral image datasets are additionally combined with calculated image data.

15. A multi-energy CT imaging method, the method comprising:
   acquiring a plurality of multispectral projection measurement datasets of an examination region of a patient;
   reconstructing a plurality of multispectral image datasets based upon the plurality of multispectral projection measurement datasets; and
   generating an image representation using the method of claim 1.

16. An image setting device, comprising:
   at least one processor configured to execute computer-readable instructions to cause the image setting device to
      receive a plurality of multispectral image datasets of an examination region of a patient, the plurality of multispectral image datasets obtained by reconstruction based on multispectral projection measurement datasets,
      automatically identify a structure to be examined based on the plurality of multispectral image datasets, and
      automatically combine differently weighted ones of the plurality of multispectral image datasets such that contrast between the structure to be examined and an environment of the structure to be examined is increased as compared to a uniform weighting.

17. A computed tomography system, comprising:
   a scanner to acquire a plurality of multispectral projection measurement datasets of an examination region of a patient;
   a control device to control the scanner and to generate a plurality of multispectral image datasets based on the plurality of multispectral projection measurement datasets; and
   the image setting device of claim 16.

18. A non-transitory computer program product including a computer program, which is directly loadable into a memory of a computed tomography system, the computer program including program sections that cause the computed tomography system to perform the method of claim 1 when the computer program is executed on the computed tomography system.

19. A non-transitory computer-readable medium storing program sections that cause a computer to perform the method of claim 1 when the program sections are executed by the computer.

20. A method for setting a contrast of a multi-energy CT image representation, the method comprising:
   receiving a plurality of multispectral image datasets of an examination region of a patient;
   automatically identifying a structure to be examined based on the plurality of multispectral image datasets; and
   automatically combining differently weighted ones of the plurality of multispectral image datasets such that contrast between the structure to be examined and an environment of the structure to be examined is increased as compared to a uniform weighting, wherein
      the automatically combining of the differently weighted ones of the plurality of multispectral image datasets is determined based on a learning system, and
      the learning system is trained by corrections by a user.

* * * * *